United States Patent [19]

Kletzky et al.

[11] Patent Number: 5,195,964
[45] Date of Patent: Mar. 23, 1993

[54] TRANSCERVICAL CATHETERIZATION CANNULA

[75] Inventors: Oscar A. Kletzky, Beverly Hills; Timothy M. Koci, Redondo Beach; Fredrick P. Torres, Sherman Oaks, all of Calif.

[73] Assignee: Research and Education Institute, Inc., Torrance, Calif.

[21] Appl. No.: 804,230

[22] Filed: Dec. 5, 1991

[51] Int. Cl.⁵ .............................................. A61B 17/34
[52] U.S. Cl. ..................................... 604/55; 604/264; 604/278
[58] Field of Search .................. 604/164, 165-170, 604/264, 190, 55, 278; 128/3, 4

[56] References Cited

U.S. PATENT DOCUMENTS

| | | | |
|---|---|---|---|
| 4,000,743 | 1/1977 | Wesner | 606/119 |
| 4,585,438 | 4/1986 | Makler | 604/55 |
| 4,606,336 | 8/1986 | Zeluff | 604/55 |
| 4,700,701 | 10/1987 | Montaldi | 604/55 |
| 4,997,419 | 3/1991 | Lakatos et al. | 606/190 |

OTHER PUBLICATIONS

LaBerge, Fallopian Tube Catheterization: Modified Fluoroscopic Technique, Oct. 24, 1989, 283 & 284.

Primary Examiner—C. Fred Rosenbaum
Assistant Examiner—Manuel Mendez

[57] ABSTRACT

The invention is a single use transcervical catheterization cannula retained by forceps for use with a catheter wire and radiopaque dye fluid. The cannula has a flexible shaft portion, an acorn to seat with the cervical canal, a fluid/catheter wire access port, and a handle member which is rotatably and axially movable on the shaft of the cannula but which can be locked at a desired position on the shaft of the cannula. A notch on a wing of the handle member engages with forceps to hold the cannula in liquid tight contact with the cervical canal. Extending beyond the end of the acorn is a curved tip, through whose open end the catheter wire is extended.

24 Claims, 2 Drawing Sheets

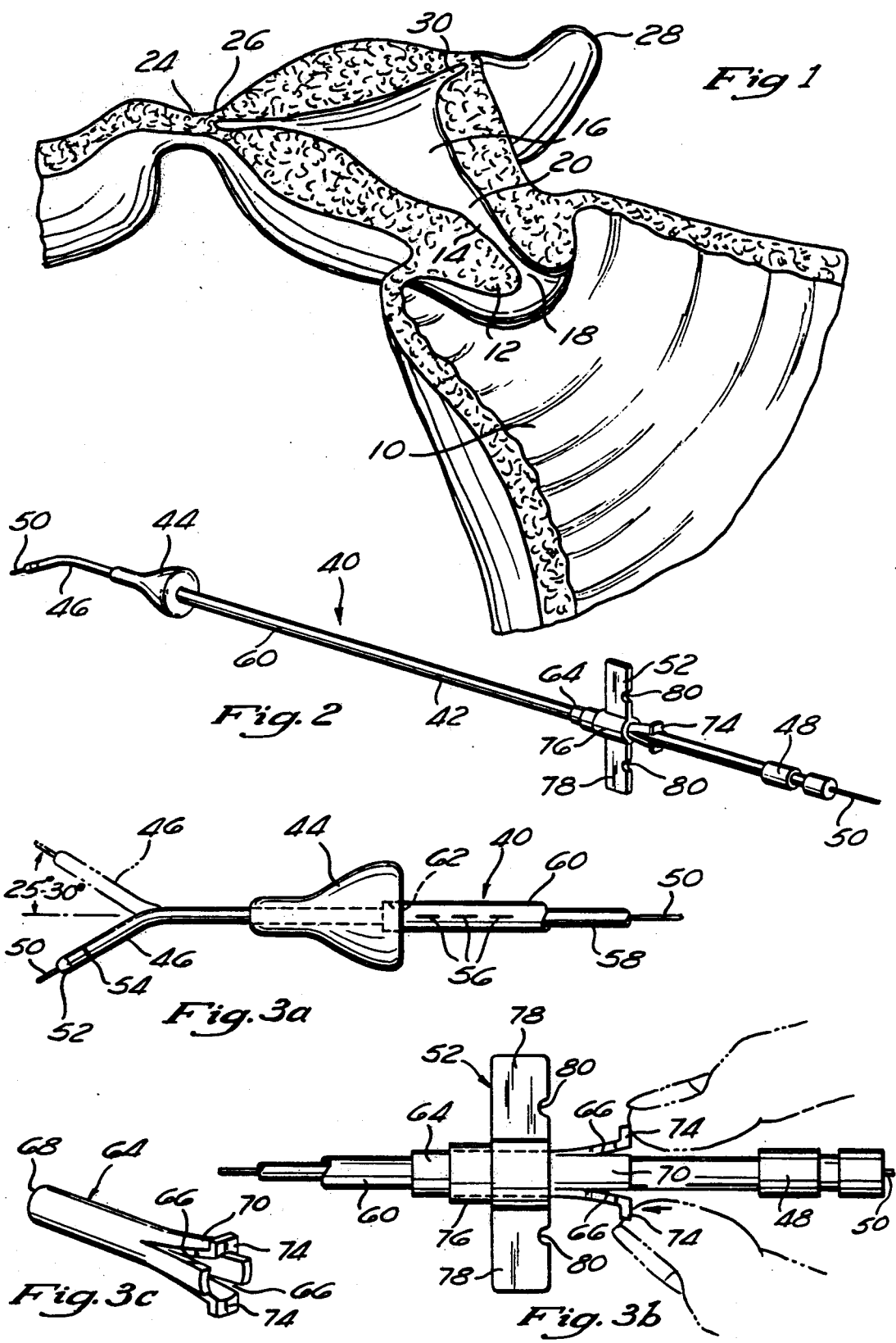

TRANSCERVICAL CATHETERIZATION CANNULA

The invention relates to single use transcervical catheterization cannulas for use in performing various procedures including the catheterization of blocked fallopian tubes.

DESCRIPTION OF THE PRIOR ART

In the performance of many transcervical procedures, the uterine cavity must be filed with a radiopaque dye fluid in order to examine the uterine cavity and associated structures such as the fallopian tubes with a fluoroscope.

In the case of blocked fallopian tubes, the point of blockage can readily be determined as the point beyond which the radiopaque dye fluid does not flow. During the catheterization procedure, the uterine cavity and fallopian tubes are first filled with the radiopaque dye fluid. A catheter wire is then passed, with the aid of a transcervical catheterization cannula, through the patient's vagina, through her cervical canal, into her uterine cavity, and finally into the fallopian tube. It is the action of the catheter wire which actually accomplishes the unblocking function.

In order to ensure that the radiopaque dye fluid remains in the uterine cavity and fallopian tubes during the catheterization procedure, and to help properly guide and support the catheter wire, various types of cannulas have been utilized. With all of the prior art devices, the cannulas are positioned to provide a liquid-tight seal with the cervical canal prior to the insertion of the catheter.

The prior art cervical cannulas achieve the needed liquid-tight cervical canal-cannula positioning by a variety of approaches. One such cannula, the Bard ® Cervical Cannula, has a pair of inflatable balloons located on the shaft of the cannula. The shaft of the cannula is forced through the cervical canal and is positioned so that one balloon lies on the inside opening of the cervical canal (termed the "internal os") and one balloon lies on the outside opening of the cervical canal (termed the "external os"). Once the Bard ® Cannula is positioned, the two balloons are inflated, liquid-tightly clamping the cannula in place in the cervical canal. However, due to the sizing requirements of the shaft carrying the balloons, the cannula must have a relatively large shaft diameter. The relatively large shaft is difficult for the operating physician to insert through the cervical canal, and as a result, considerable pain and discomfort is caused to the patient.

Another device, disclosed in U.S. Pat. No. 3,385,300 to Holter, depends on a helically threaded cone to provide the desired liquid-tight cervical canal-cannula seal. The Holter threaded cone is literally "threaded" into the cervical canal. Although the seal thus established is satisfactory, the Holter device is very painful for the patient and causes trauma to the cervix and therefore its use has long been discontinued.

A third type of cannula, the Thurmond-Rösch Movable Cup Hysterocath T.M., manufactured by Cook Incorporated, sealably engages a cone (called an "acorn") positioned on the distal end of its shaft with the os externum by means of a sliding vacuum cup connected to a vacuum port. Once the vacuum cup is evacuated, it seals with the cervix, pushing the acorn into the os externum. One major problem with this type of device is that due to a not infrequent mismatch between the size of the cup and the size of the os externum, it is often difficult to achieve the desired liquid-tight cervical-canal-cannula seal. Another drawback to this device is that it must be used with a leading catheter passed through the cannula. It is the leading catheter which is used to aim the catheter wire towards the blocked fallopian tube. This results in a larger sized cannula shaft being required, which is in turn sometimes difficult to insert through the cervical canal.

A fourth type of device is disclosed in U.S. Pat. No. 4,775,362, to Kronner establishes the liquid-tight cervical canal-cannula seal by combining a balloon to be inflated on the interior os with a slidable cup to seat on the os externum. The Kronner device suffers from problems similar to the Thurmond-Rösch Movable Cup Hyterocath T.M.

Lastly, the Cohen self-retaining cannula in somewhat similar in appearance to the invention of this application, although it is only used to flood the uterine cavity with a radiopaque dye fluid, and is not used to guide a catheter wire. The liquid tight seal is established by seating an acorn located on the cannula's shaft firmly into the os externum. The Cohen device has a spring-loaded forceps holding handle on its shaft. A pair of tenaculum forceps is clamped onto the exterior of the cervix and the locking flats of the forceps are engaged with the forceps holding handle. The spring force provided by the spring-loaded handle forces the acorn tightly into the cervical canal.

SUMMARY OF THE INVENTION

There is a need for a disposable, single use transcervical catheterization cannula which is relatively painless for the patient, yet which provides a liquid-tight cervical canal-cannula seal and which is easy to insert into the cervical canal and easily manipulated once it is placed therein. It is also preferably for such a device to be relatively inexpensive to manufacture.

From the foregoing, it can be seen that an object of the present invention is to provide a transcervical catheterization cannula retained by forceps and for use with a catheter wire and radiopaque dye fluid, comprising:

an elongate shaft member having a proximal end and a distal end and having at least one lumen passing therethrough through which the catheter wire and the fluid can pass;

a tip means provided at said distal end of said shaft member, said tip member being in communication with said at least one lumen and being open at its distal end;

a cervical canal seating member positioned on said shaft rearward of said tip means; and a handle member which is rotatable and axially movable on said shaft, said handle member being located rearward of said abutting member and having a locking means allowing said handle to be axially and rotatably locked on said shaft, said handle member being adjustable to positively engage with the forceps clamped to the patient's cervix to thereby cause said cervical canal member to liquid-tightly engage with the patient's cervical canal, yet allow said shaft member, said sealing member and said tip means to rotate relative to the cervical canal.

Another object of the invention is to provide a transcervical catheterization cannula retained by forceps and for use with a catheter wire and radiopaque dye fluid, comprising:

an elongate shaft member having a proximal end and a distal end and having a lumen therethrough through which the catheter wire and the fluid can pass;

a curved tip positioned at said distal end of said shaft member, said tip member being in communication with said lumen, said tip means being opened at its distal end;

a cervical canal seating member positioned on said shaft rearward o said curved tip; and a handle member which is rotatably and axially movable on said shaft, said handle member being located rearward of said abutting member and having a locking means allowing said handle member to be axially and rotatable locked on said shaft, said handle member being adjustable to positively engage with forceps clamped to the patient's cervix to thereby cause said cervical canal seating member to engage with the patient's cervical canal, yet allow said shaft member, said seating member, and said tip means to rotate relative to the cervical canal.

Yet another object of the invention is to provide a transcervical catheterization cannula retained by forceps and for use with a catheter wire and radiopaque dye fluid, comprising:

an elongate shaft member having a proximal end and a distal end and having a lumen therethrough through which the catheter wire and the fluid can pass;

a curved tip positioned at said distal end of said shaft, said tip means being opened at its proximal end;

a cervical canal seating member positioned on said shaft rearward of said curved tip; and a handle member which is rotatably and axially movable on said shaft member, said handle member being located rearward of said abutting member, said handle member comprising an elongate tubular sleeve member with an inner diameter slightly larger than the outer diameter of said shaft member, said sleeve member being slideably positioned on said shaft member, said tubular sleeve member having an outer diameter which is smaller at its distal end than at its proximal end, said tubular member having at least one elongate slit passing longitudinally through said proximal end of said sleeve, and a collar member having an inner diameter slightly larger than the outer diameter of said sleeve member at its distal end but smaller than the outer diameter of said sleeve member at its proximal end, said collar member having at least one wing member extending outwardly from said collar member, said wing members having a notch means to engage with the forceps to thereby cause said cervical canal sealing member to engage with the patient's cervical canal, whereby said handle member can be locked at its desired axial and radial position relative to the shaft member by sliding said collar member rearwardly onto said sleeve member, thereby causing said collar member to compress said proximal end of said sleeve member to frictionally engage and grip said elongate shaft member, thereby locking said handle member on said shaft member.

Other objects of the invention and advantages of the invention will be apparent as the description proceeds.

BRIEF SUMMARY OF THE INVENTION

In accordance with the illustrated embodiment of the present invention, a cannula is provided which can be liquid-tightly engaged with the cervical canal, yet which can be rotated while in place to properly position the tip of the cannula so that the catheter inserted therethrough will have proper angle of attack to gain entrance to the fallopian tube which is to be unblocked by the catheterization procedure.

In a preferred embodiment of the invention, a forceps holding handle is provided which relies on a friction sleeve to set the handle's position on the cannula's shaft.

BRIEF DESCRIPTION OF THE DRAWINGS

In describing the invention, reference will be made to the accompanying drawings wherein:

FIG. 1 is a partially exposed view of a human female reproductive system;

FIG. 2 is a perspective view of a first embodiment of the device;

FIG. 3a is a close-up view of the distal end of the device showing the curved tip with the catheter wire partially extending therethrough, the acorn, and the outer and inner tubes of the cannula's shaft;

FIG. 3b is a side view of the handle member of the first embodiment of the invention;

FIG. 3c is a perspective view of the sleeve member of the handle of the first embodiment;

DETAILED DESCRIPTION OF THE PREFERRED EMBODIMENT

Figure 4:
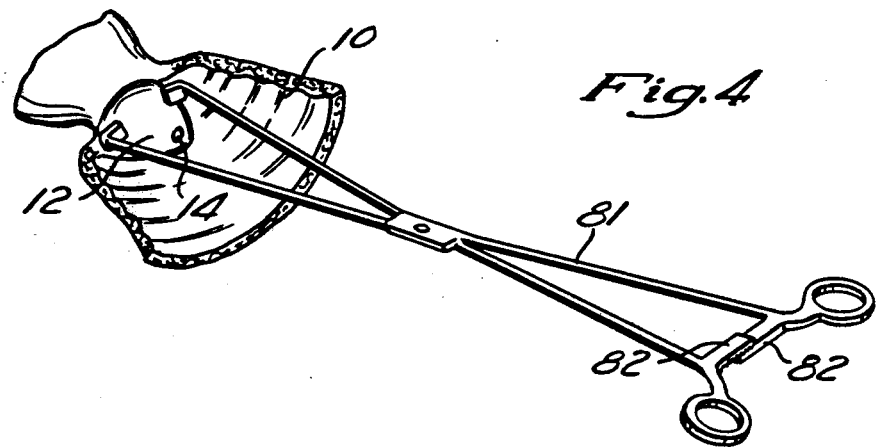
FIG. 4 is a perspective view of a pair of tenaculum forceps gripping the cervix.

Referring to the drawings, there is illustrated in FIG. 1 a partially exposed view of a human female's internal reproductive system. The vaginal cavity 10 communicates with the cervix 12, through which the cervical canal 14 passes into the uterine cavity 16. The outer opening of the cervical canal 14 is the os externum 18 and the inner opening of the cervical canal 14 is the internal os 20. The uterine cavity 16 although shown in an expanded shaped, is actually normally a virtual cavity wherein the uterus walls 22 are in contact with each other. However, when the uterine cavity is filled with a fluid, the uterine walls 22 move away from each other.

At the upper end of the uterine cavity 16 the fallopian tubes 24 merge with the uterine cavity at a portion called the isthmus 26. Each fallopian tube 24 is approximately four inches in length and connects with the ovaries 28 via the passages 30 through the fallopian tubes 24.

The fallopian tubes 24 are sometimes blocked by scarring, tissue build up, or for some other reason, thereby preventing the ova from being conveyed down the fallopian tubes 24 into the uterine cavity, thereby causing some forms of female sterility. Transcervical catheterization of blocked fallopian tubes is sometimes effective in reversing these forms of sterility.

FIG. 2 is a perspective view of a preferred embodiment of the transcervical catheterization cannula 40. The elongate cannula shaft 42 has at least one passage passing therethrough and has a cervical canal seating member, called an acorn 44, located at its distal end. As best shown in FIG. 3a, the cannula shaft 42 includes an inner tube 58 which passes through and fits inside an outer tube 60. The curved tip member 46 comprises the portion of the inner tube 58 which extends beyond the distal end of the acorn 44. Fixed at the proximal end of the cannula shaft 42 is an access and injection port 48, such as a Tuohy-Borst adapter. The access and injection port 48 can be connected to a supply of radiopaque dye fluid and will also allow a catheter wire 50 to slide therethrough without permitting the fluid to leak out through the cannula. A handle member 52 on the cannula shaft can be positioned at a desired axial and radial position on the cannula shaft 42. The entire cannula is about 14 inches long from end to end.

FIG. 3a is a close-up view of the distal end of the cannula 40. The acorn 44 is made of semi-rigid silicone rubber or other plastics. It is symmetrical about its radial axis and is curved downwards from its proximal end to its distal end to gently meet the proximal end of the tip member 46. The tip member 46 is curved at approximately a 25 to 30 degree angle to the cannula shaft 42, such, a range of curvature being found to be ideal to guide the catheter wire 50 into the fallopian tube 24. The catheter wire 50 extends through the open distal end 52 of the tip member 46. Located near the end 52 of the tip member 46, a radiopaque marker 54, such as a band of platinum wire, may be positioned to aid the operating physician in determining the position of the open tip 52. As an additional aid in properly orienting the tip member 46, visual indication marks 56, such as a number of dash marks, can be put on the cannula shaft 42.

As stated above, and as shown in FIG. 3a, the cannula shaft 42 includes an inner tube 58 which fits inside an outer tube 60. Both the inner and outer tubes 58 and 60 are ideally made of flexible material, such as nylon. The catheter wire 50 slides through the interior of the inner tube 58, as does the fluid which is used fill the uterine cavity and fallopian tubes. The outer tube 60 can partially enter a receiving hole 62 formed in proximal end of the acorn to hold the acorn 44 in place. In addition, cement or glue can be used. The inner tube 58 passes through the axis of the acorn 44 and the part in front of the distal end of the acorn 44 defines the curved tip member 46. The purpose of the outer tube 60 is to increase the rigidity of the cannula shaft 42 while still allowing it to have some flexibility. The tip member 46 is rounded at its open end 52 so as to avoid injury to cervical canal 12, uterine cavity 16 and fallopian tubes 24 during the procedure.

FIG. 3b is a side view of the preferred embodiment of the handle member 52. The handle member 52 has an elongate sleeve member 64 with at least one slit 66 in its wall at a proximal end of the sleeve 64. FIG. 3c is a perspective view of the sleeve member 64. The sleeve member 64 is sized so that its outer diameter at its distal end 68 is smaller than its outer diameter at its proximal end 70. The inner diameter the sleeve 64 is slightly greater than the outer diameter of outer tube 60 so that the sleeve member 64 can normally slide on the outer tube 60. If desired, finger grips 74 can be positioned at the proximal end of the sleeve member 64 in the vicinity of the slits 66 to aid the gripping and positioning the sleeve member 64. A collar member 76 with a pair of wings 78 is slideably engageable around the outside of the sleeve member 64. The inner diameter of the collar member 76 is larger than the outer diameter of the sleeve member at its distal end 68 but smaller than the outer diameter of the sleeve member at its proximal end 70. Thus, as the proximal portion of the collar member 76 and proximal end 70 of the sleeve member 64 are brought closer together, the collar member 76 compresses the proximal end 70 of the sleeve member 64, particularly the region of the sleeve member with slits 66, causing the collar member 76, sleeve member 64 and cannula shaft 42 to frictionally engage with each other, thereby locking the handle member 52 at a desired axial and radial position on the cannula shaft 42. The cannula shaft 42 and its associated acorn 44 and its curved tip member 46, however, can be rotated relative to the handle member 52 by twisting the cannula shaft 42, thereby allowing the curved tip member 46 to be precisely directed by the physician. On the rearwardly facing edges of each of the pair of wings 78, a notch 80 is provided. As will be discussed in further detail below, the notch 80 serves as a catch to engage with the locking flats of tenaculum forceps.

Figure 5:
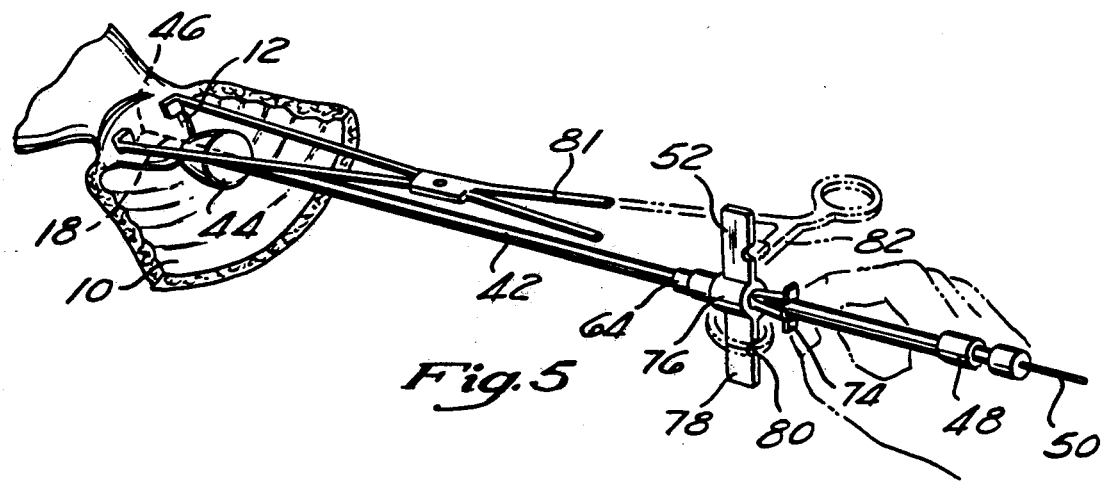
FIG. 5 is a perspective view of a first embodiment in use with tenaculum forceps.

FIGS. 4 and 5 show a pair of tenaculum forceps 81 clamped onto the cervix 12. The tenaculum forceps have a pair of locking flats 82. The physician wishing to perform a transcervical fallopian tube catheterization procedure first inserts the transcervical catheterization cannula through the vagina (not shown) and inserts the tip member 46 through the cervical canal 14 and gently positions the acorn 44 so that it seats with the os externum 18. Due to the flexibility of the cannula shaft 42, the cannula shaft 42 can be flexed to aid in inserting the tip member 46 into the cervical, canal 14. Thereafter, a pair of tenaculum forceps 81 are clamped on the cervix 12 to secure them in place and the locking flats 82 of the forceps 81 are engaged. The handle member 52 is then positioned so that one of the notches 80 on one of the rearwardly facing edges of the wings 78 catch the locking flats 82.

By moving the handle member 52, rearwards and locking it in place, the tenaculum forceps 81 exerts a pulling force on the handle member 52, which is translated via the cannula shaft 42 to the acorn 44, thereby establishing a liquid-tight seal between the acorn 44 and the os externum 18.

Once the transcervical catheterization cannula is positioned, the physician can fill the uterine cavity 16 and the fallopian tubes 2 to the extent possible with the radioscopy fluid or dye via the inner tube 58. The access and injection port 48 allows the fluid to be first injected, the fluid access to be shut off, and then the catheter wire 50 to be slid through the access and injection port 48 through the inner tube 58 and out the opening 52 in the curved tip member 46, all while the fluid remains in the uterine cavity 16. During the transcervical catheterization procedure, the physician monitors the position of the transcervical catheterization cannula 40, the catheter wire 50 and the inner confines of the uterine cavity 16 and fallopian tubes 26 by a fluoroscope or other means. The radiopaque marker 54 located near the opening 52 of the curved tip member 46 shows up on the fluoroscope, which helps to indicate the position of the tip 52 in relationship to the isthmus 26 of the fallopian tubes 24. This, in connection with the visual indication mark 56 on the surface of the cannula shaft 42 greatly aids the physician in determining the optimum angle of attack necessary for the catheter wire 5 to easily enter the blocked fallopian tube 24. During the procedure, the handle member 52 and rear half or so of the cannula shaft 24 remains outside of the patient's body.

Due to the ability of the handle member 52 to be rotated relative to the cannula shaft 42 and its associated acorn 44 and the tip member 46, the physician can easily rotate the cannula shaft 42 and its associated acorn 44 seating on the os externum 18 relative to the handle member 52 and the tenaculum forceps 80 clamped on to the cervix in order to change the angle of attack of the tip member 46, all without having to the tenaculum forceps 81 from the cervix 12 and reclamp clamp them after the desired angle of attack has been attained. Obviously, the ability to easily change the angle of attack without having to repeatedly clamp and unclamp the tenaculum forceps 81 for the cervix 12 makes the transcervical catheter procedure less unpleasant and painful for the patient, and easier and quicker for the operating physician.

It should be borne in mind that the drawings are not rendered in actual scale so that certain features of the invention can be brought out and depicted.

The drawings and the foregoing description are not intended to represent the only form of the invention in regard to the details of its construction and manner of operation. In fact, it will be evident to one skilled in the art that modifications and variations may be made without departing from the spirit and scope of the invention. Changes in form and in the proportion of parts, as well as the substitution of equivalents, are contemplated as circumstances may suggest or render expedient; and although specific terms have been employed, they are intended in a generic and descriptive sense only and not for the purpose of limitation, the scope of the invention being delineated in the following claims:

I claim:

1. A transcervical catheterization cannula retained by forceps and for use with a catheter wire and radiopaque dye fluid, comprising:
    an elongate shaft member having a proximal end and a distal end and having at least one lumen passing therethrough through which the catheter wire and the fluid can pass;
    a curved tip means curved relative to the axis of said elongate shaft member means provided at and extending beyond said distal end of said shaft member, said tip means being in communication with said at least one lumen and being open at its distal end;
    a cervical canal seating member positioned on said shaft rearward of said tip means; and
    a handle member which is rotatable and axially movable on said shaft member, said handle member being located rearward of said cervical canal seating member and having a locking means allowing said handle to be axially and rotatably locked on said shaft member, said handle member being axially and rotatably adjustable to positively engage with the forceps clamped to the patient's cervix to thereby cause said cervical canal member to liquid-tightly engage with the patient's cervical canal, while permitting said elongate shaft member, said cervical canal seating member and said curved tip means to be selectively axially rotated as a unit relative to the cervical canal in order to aim the curved tip towards the patient's fallopian tube so as to permit the catheter wire to enter the fallopian tube.

2. The transcervical catheterization cannula of claim 1, wherein said shaft member comprises an inner tube positioned at least partially in the interior of an outer tube, the catheter wire and the fluid passing through said inner tube.

3. The transcervical catheterization cannula of claim 2, wherein said inner and outer tubes are flexible plastic tubes.

4. The transcervical catheterization cannula of claim 3, wherein said tip means comprises a portion of said inner tube which extends distally beyond said cervical canal seating member and said outer tube.

5. The transcervical catheterization cannula of claim 1 further comprising a fitting member positioned on said proximal end of said shaft member, said fitting member being adapted to connect with a supply of the radiopaque dye fluid and also to slideably, but liquid-lightly, receive the catheter wire therethrough.

6. The transcervical catheterization cannula of claim 1, wherein said cervical canal seating member is radially uniform in shape and has an outer surface with a curvature decreasing from the proximal end to the distal end of said seating member to gently join with said tip means.

7. The transcervical catheterization cannula of claim 1, wherein said handle member comprises:
    an elongate tubular sleeve member with an inner diameter slightly larger than the outer diameter of said elongate shaft, said elongate tubular sleeve member being slideably positionable on said elongate shaft, said elongate tubular sleeve member having an outer diameter which is smaller at its distal end than at its proximal end, said elongate tubular sleeve member having at least one elongate slit passing longitudinally through said proximal end of said elongate tubular sleeve member; and
    a collar member having an inner diameter slightly larger than the outer diameter of said sleeve member at its distal end but smaller than the outer diameter of said sleeve member at its proximal end, said collar member having at least one wing member extending outwardly from said collar member, said at least one wing member having a notch means to engage with the forceps, whereby said handle member can be locked at a desired axial and radial position relative to the elongate shaft by sliding said collar member rearwardly onto said sleeve member, thereby causing said collar member to compress said proximal end of said sleeve member to frictionally engage and grip said elongate shaft, thereby locking said handle member on said shaft member.

8. The transcervical catheterization cannula of claim 1, wherein said tip means is curved and has an open distal end, thereby allowing the catheter wire to pass therethrough in a curved path and enter a fallopian tube of a patient at a desired angle of attack.

9. The transcervical catheterization cannula of claim 3, wherein said tip means is curved and has an open distal end, thereby allowing the catheter wire to pass therethrough in a curved path and enter a fallopian tube of a patient at a desired angle of attack.

10. The transcervical catheterization cannula o claim 9, wherein said tip means has a radiopaque marker positioned near its distal end.

11. The transcervical catheterization cannula of claim 10, wherein said elongate shaft has visible indication marks located on its surface to indicate the direction in which said tip means is pointed.

12. A transcervical catheterization cannula retained by forceps and for use with a catheter wire and radiopaque dye fluid, comprising:
    an elongate shaft member having a proximal end and a distal end and having a lumen therethrough through which the catheter wire and the fluid can pass, said shaft member comprising an inner tube positioned at least partially in the interior of an outer tube, the catheter wire and the fluid passing through said inner tube;

a curved tip means positioned at and extending beyond said distal end of said shaft member, said tip means being opened at its distal end;

a cervical canal seating member positioned on said shaft rearward of said curved tip means said tip means comprising the portion of said inner tube which extends distally beyond said cervical canal seating member and said outer tube; and a handle member which is rotatably and axially movable on said shaft, said handle member being located rearward of said cervical canal seating member and having a locking means allowing said handle member to be axially and rotatably locked on said shaft, said handle member being adjustable to positively engage with forceps clamped to the patient's cervix to thereby cause said cervical canal seating member to engage with the patient's cervical canal, yet allow said shaft member, said seating member, and said tip means to be selectively rotated as a unit relative to the cervical canal in order to permit the curved tip means to be precisely aimed towards the patient's fallopian tube so as to permit the catheter wire to enter the fallopian tube.

13. The transcervical catheterization cannula of claim 12, wherein said inner and outer tubes are flexible plastic tubes.

14. The transcervical catheterization cannula of claim 12, further comprising a fitting member positioned on said proximal end of said shaft member, said fitting member being adapted to connect with a supply of radiopaque dye fluid and also to slideably, but liquid-tightly, receive the catheter wire therethrough.

15. The transcervical catheterization cannula of claim 12, wherein said handle member comprises:

an elongate tubular sleeve member with an inner diameter slightly larger than the outer diameter of said shaft member, said sleeve member being slideably positionable on said shaft member, said sleeve member having an outer diameter which is smaller at its distal end than at its proximal end, said sleeve member having at least one elongate slit passing longitudinally through said proximal end of said sleeve member; and a collar member having an inner diameter slightly larger than the outer diameter of said sleeve member at its distal end but smaller than the outer diameter of said sleeve member at its proximal end, said collar member having at least one wing member extending outwardly from said collar member, said wing members having a notch means to engage with the forceps, whereby said handle member can be locked at a desired axial and radial position relative to said shaft member by sliding said collar member rearwardly onto said sleeve member, thereby causing said collar member to compress said proximal end of said sleeve member to frictionally engage and grip said shaft member, thereby locking said handle member on said shaft member.

16. The transcervical catheterization cannula of claim 12, wherein said tip means has a radiopaque marker positioned near its distal end.

17. The transcervical catheterization cannula of claim 12, wherein said shaft member has visible indication marks located on its surface to indicate the direction in which said tip means is pointed.

18. A transcervical catheterization cannula retained by forceps and for use with a catheter wire and radiopaque dye fluid, comprising:

an elongate shaft member having a proximal end and a distal end having a lumen therethrough through which the catheter wire and the fluid can pass;

a curved tip means positioned at said distal end of said shaft, said tip means being opened at its proximal end;

a cervical canal seating member positioned on said shaft rearward of said curved tip; and a handle member which is rotatably and axially movable on said shaft member, said handle member being located rearward of said cervical canal seating member, said handle member comprising an elongate tubular sleeve member with an inner diameter slightly larger than the outer diameter of said shaft member, said tubular sleeve member being slideably positioned on said shaft member, said tubular sleeve member having an outer diameter which is smaller at its distal end than at its proximal end, said tubular sleeve member having at least one elongate slit passing longitudinally through said proximal end of said sleeve, and a collar member having an inner diameter slightly larger than the outer diameter of said sleeve member at its distal end but smaller than the outer diameter of said sleeve member at its proximal end, said collar member having at least one wing member extending outwardly from said collar member, said wing members having a notch means to engage with the forceps to thereby cause said cervical canal sealing member to engage with the patient's cervical canal, whereby said handle member can be locked at its desired axial and radial position relative to the shaft member by sliding said collar member rearwardly onto said sleeve member, thereby causing said collar member to compress said proximal end of said sleeve member to fictionally engage and grip said elongate shaft member, thereby locking said handle member on said shaft member, yet permitting said handle member to be selectively rotated relative said elongate cannula shaft to orient the positioning of said curved tip means.

19. The transcervical catheterization cannula of claim 18, wherein said elongate shaft member comprising an inner tube positioned at least partially in the interior of an outer tube, said catheter and said fluid passing through said inner tube.

20. The transcervical catheterization cannula of claim 19, wherein said inner and outer tubes are flexible plastic tubes.

21. The transcervical catheterization cannula of claim 20, wherein said tip means comprises a portion of said inner tube which extends distally beyond said cervical canal seating member and said outer tube.

22. The transcervical catheterization cannula of claim 21, wherein said cervical canal seating member is radially uniform in shape and has an outer surface with a curvature decreasing from the proximal end to the distal end of said member to gently join with said tip means.

23. The transcervical catheterization cannula of claim 22, wherein said tip means has a radiopaque marker positioned near its distal end.

24. The transcervical catheterization cannula of claim 23, wherein said shaft member has visual indication marks located on its surface to indicate the direction in which said tip means is pointed.

* * * * *